(12) United States Patent
Nakagawa et al.

(10) Patent No.: US 9,417,235 B2
(45) Date of Patent: *Aug. 16, 2016

(54) OPTICAL MEASUREMENT APPARATUS

(75) Inventors: Takashi Nakagawa, Kyoto (JP); Shinya Nakajima, Kyoto (JP); Tokuo Kasai, Kyoto (JP); Kyouichi Ohshiro, Kyoto (JP)

(73) Assignee: ARKRAY, Inc., Kyoto-shi (JP)

( * ) Notice: Subject to any disclaimer, the term of this patent is extended or adjusted under 35 U.S.C. 154(b) by 348 days.

This patent is subject to a terminal disclaimer.

(21) Appl. No.: 12/593,074

(22) PCT Filed: Nov. 20, 2008

(86) PCT No.: PCT/JP2008/071139
§ 371 (c)(1),
(2), (4) Date: Sep. 25, 2009

(87) PCT Pub. No.: WO2010/058472
PCT Pub. Date: May 27, 2010

(65) Prior Publication Data
US 2011/0058995 A1    Mar. 10, 2011

(51) Int. Cl.
| | |
|---|---|
| *G01N 21/84* | (2006.01) |
| *G01N 21/25* | (2006.01) |
| *C12M 1/34* | (2006.01) |
| *G01N 33/52* | (2006.01) |
| *G01N 33/543* | (2006.01) |
| *G01N 33/558* | (2006.01) |
| *G01N 33/50* | (2006.01) |

(52) U.S. Cl.
CPC .......... *G01N 33/54386* (2013.01); *G01N 21/25* (2013.01); *G01N 21/8483* (2013.01); *G01N 33/52* (2013.01); *G01N 33/558* (2013.01); *Y10T 436/11* (2015.01); *Y10T 436/12* (2015.01)

(58) Field of Classification Search
None
See application file for complete search history.

(56) References Cited

U.S. PATENT DOCUMENTS

| | | | | |
|---|---|---|---|---|
| 4,023,930 A | * | 5/1977 | Blunck et al. | ................. 436/44 |
| 5,077,010 A | * | 12/1991 | Ishizaka et al. | ............... 422/408 |
| 5,316,727 A | | 5/1994 | Suzuki et al. | |
| 5,597,532 A | * | 1/1997 | Connolly | ............... B01L 3/545 |
| | | | | 422/401 |
| 5,885,839 A | | 3/1999 | Lingane et al. | |

(Continued)

FOREIGN PATENT DOCUMENTS

| | | |
|---|---|---|
| CN | 1304490 A | 7/2001 |
| EP | 0922954 A2 | 6/1999 |

(Continued)

*Primary Examiner* — Neil N Turk
(74) *Attorney, Agent, or Firm* — Fox Rothschild LLP

(57) ABSTRACT

An object is to provide an optical measurement apparatus for performing an efficient test by optical measurement without incurring incorrect measurements.
To this end, the measurement apparatus utilizes a test instrument mounted thereto and including a carrier with a reagent retaining portion for application of a sample. The measurement apparatus includes a reader for color development at the reagent retaining portion, and a controller for driving control of the reader and for required determination. The controller performs the determination by utilizing the data obtained by reading the color development of the reagent after a reaction completion period Tr1-Tr6 depending on the reagent and starting from the mounting of the test instrument. When detecting that the color development at the reagent retaining portion is completed before the lapse of the reaction completion period Tr1-Tr6 after the mounting of the test instrument, the controller stops the test for the test instrument.

7 Claims, 10 Drawing Sheets

(56) References Cited

U.S. PATENT DOCUMENTS

| | | |
|---|---|---|
| 2004/0173456 A1 | 9/2004 | Boos et al. |
| 2006/0246596 A1 | 11/2006 | Jaunakais |
| 2007/0188736 A1* | 8/2007 | Fouquet ............ G01N 21/8483 356/39 |
| 2008/0019871 A1 | 1/2008 | Sakamoto et al. |

FOREIGN PATENT DOCUMENTS

| | | |
|---|---|---|
| EP | 1096256 A1 | 5/2001 |
| JP | 59-10850 | 1/1984 |
| JP | 03-95433 | 4/1991 |
| JP | 05-005736 | 1/1993 |
| JP | 08-110342 | 4/1996 |
| JP | 09-127120 | 5/1997 |
| JP | 2001-318101 | 11/2001 |
| JP | 2003-004743 | 1/2003 |
| JP | 2004-317211 | 11/2004 |
| JP | 2005-502858 | 1/2005 |
| JP | 2006-250787 | 9/2006 |
| JP | 2007-107889 | 4/2007 |
| WO | 99/35487 A1 | 7/1999 |
| WO | 03/005905 | 1/2003 |
| WO | 2006/059694 | 6/2006 |
| WO | 2007/016665 A2 | 2/2007 |

* cited by examiner

京都太郎 CH1    FluA: (+)1
                FluB: —

2007/10/31 09:02-09:17
ID:1234567890123457

京都花子 CH2    FluA: +
                FluB: **

2007/10/31 09:04-09:19
ID:1234567890123458

関西太郎 CH3    FluA: (+)1
                FluB: —

2007/10/31 09:06-09:21
ID:1234567890123459

関西花子 CH4    FluA: NG
                FluB: NG

2007/10/31 09:08-09:23
ID:1234567890123460

大和太郎 CH5    FluA: —
                FluB: —

2007/10/31 09:10-09:25
ID:1234567890123491

大和花子 CH6    FluA: +
                FluB: **

OPTICAL MEASUREMENT APPARATUS

TECHNICAL FIELD

The present invention relates to an optical measurement apparatus for performing a test by reading color development of a reagent by optical measurement.

BACKGROUND ART

In recent years, in hospitals and clinics or for home medical care, optical measurement apparatuses are often used as an apparatus for POCT (Point of Care Testing), which is the testing by people other than laboratory professionals. Examples of such optical measurement apparatuses include a clinical laboratory test apparatus (see e.g. Patent Document 2) for optically reading an urine test strip dipped in and pulled out of urine (see e.g. Patent Document 1) or a biochemical test piece to which blood serum/blood plasma extracted from blood is applied, and an apparatus for measuring a cuvette (see e.g. Patent Document 3) in which a liquid reagent is sealed.

FIG. 7 shows an example of conventional optical measurement apparatus (see e.g. Patent Document 4). To the illustrated optical measurement apparatus X, a test instrument Y for immunochromatography is mounted. The test instrument Y is a test piece in the form of a strip provided with a porous carrier 91. The porous carrier includes a plurality of reagent retaining portions 92 which retain a reagent (an immunologic substance, mainly an antibody) fixed to the portion. When a liquid sample such as blood or urine to be analyzed is applied to part of the test instrument Y, the sample infiltrates into the porous carrier 91. When the sample moving through the carrier reaches the reagent retaining portions 92, the sample reacts with the reagent. As a result, the reagent retaining portions 92 develop a color in accordance with the concentration of a particular component contained in the sample.

FIG. 8 shows a typical urine test strip to be used by dipping in urine. The illustrated test strip 910 includes a base 911 in the form of a strip, and reagent retaining portions 912. Each reagent retaining portion 912 is provided on the base 911 and includes a carrier made of a porous matrix such as filter paper in which a reagent is fixed in an impregnated and dried state. When the reagent retaining portion 912 of the test strip 910 is dipped in a urine sample collected in e.g. a paper cup and pulled out, the urine sample infiltrated in the reagent retaining portion 912 through the carrier reacts with the reagent. After the lapse of a predetermined reaction period, the color development of the reagent retaining portion 912 is checked.

FIG. 9 shows an example of conventional optical measurement apparatus for the measurement of a biochemical test piece including a reagent retaining portion to which a sample of urine or blood serum/blood plasma extracted from blood is to be directly applied. The illustrated optical measurement apparatus 920 includes a table 922 on which biochemical test pieces 921 are to be mounted. Each test piece 921 includes a carrier made of at least one of a high polymer compound (e.g. paste represented by water-soluble polymer) and a porous film (such as knit fabric or nonwoven fabric). The reagent retaining portion is provided by fixing a reagent to at least one of the high polymer compound and the porous film in a dry state. To perform measurement using the optical measurement apparatus 920, a liquid sample such as blood or urine to be analyzed is directly applied to the reagent retaining portion of the test piece 921. The sample dissolves the high polymer compound forming the carrier or infiltrates into the porous film. Thus, the sample reacts with the reagent in the reagent retaining portion. After the lapse of a predetermined reaction period, the color development of the reagent retaining portion is checked.

FIG. 10 shows an example of test instrument of a cuvette type. The test instrument 930 shown in the figure includes a plurality of wells 931 and is made of e.g. a light-transmitting resin. Each of the wells 931 is used as a carrier, and a reagent retaining portion is provided by sealing a reagent in a liquid or solid state in the well 931. When a sample is put into a selected one of the wells 931 of the test instrument 930, the sample reacts with the reagent in the well 931. After a predetermined period of time, the well 931, which functions as the reagent retaining portion, develops a color in accordance with the concentration of a particular component contained in the sample. Since the well 931 transmits light, the color development is easily checked from the outside.

Referring again to FIG. 7, the optical measurement apparatus X includes a light emitting means 93 and a light receiving means 94. When the test instrument Y is mounted to the optical measurement apparatus X, an instruction to start the test is given to the controller 95 by e.g. the user's operation. The controller 95 performs the light emitting operation for lighting the light emitting means 93 and the light receiving operation for receiving the light reflected by the porous carrier 91 including the reagent retaining portion 92 at the light receiving means 94. By the signal transmission from the light receiving means 94 to the controller 95, the image data of the reagent retaining portions 92 of the porous carrier 91 are stored in the controller 95. By analyzing the image data which corresponds to the color development of the reagent retaining portions 92, the presence or absence of a particular component in the sample is determined.

Though not illustrated, when the test instrument Y is an urine test strip similar to the test strip 910 shown in FIG. 8 or a biochemical test piece, the light reflection during or after the reaction of the sample with the reagent on the surface of the reagent retaining portion 912 (sometimes called a reagent pad) is measured by an exclusive device. When the test instrument Y is of a cuvette-type similar to the test instrument 930 shown in FIG. 10, the light reflection or light transmission after the reaction of the sample with the reagent in the well is measured through the light-transmitting surface of the well.

The test results obtained by the optical measurement are outputted by an output means 96 such as a printer. Based on the output results, the user can recognize the presence or absence of a particular component in the sample.

After a sample is applied to the test instrument Y, it takes some time before the reaction progresses to such a degree that proper testing is possible, and this reaction completion period varies depending on the kind or amount of the reagent. Thus, after the sample is applied to the test instrument Y, the user needs to measure the time until the testing by e.g. the optical measurement apparatus X becomes possible. To avoid this, the optical measurement apparatus shown in FIG. 9 is designed to automatically perform the pipetting, i.e., application of the sample to the test piece 921, the measurement of time and the measurement of the color development after the lapse of the reaction time. Thus, the user just needs to put an unused test piece 921 and a container containing a sample into the optical measurement apparatus 920.

However, in e.g. a simple measurement apparatus without a pipetting function or a small measurement apparatus in which a sample obtained from a patient is not to be stored, the test instrument Y does not automatically apply the sample to the test instrument Y. To use such a measurement apparatus, as described above, the user needs to apply the sample to the test instrument Y manually (by dipping in the case of a urine test strip or dropping using a pipette in the case of a test piece or a cuvette) and then mount the test instrument Y to the measurement apparatus. To manually apply the sample to the test instrument Y and further measure the time is a burden on the user.

For instance, tests for influenza by immunochromatography may need to be performed with respect to a large number of patients in one hospital in a short period of time. In such a case, samples obtained from the large number of patients may be applied to test instruments Y at different timings, and the reaction completion period needs to be measured with respect to each of the test instruments. Further, to smoothly perform the testing of the test instruments Y, the timing of application of the sample to each test instrument Y needs to be varied intentionally.

In tests for allergy by immunochromatography, each patient may be tested for a plurality of allergy items. In such a case, a sample obtained from one patient is applied to a plurality of test instruments Y. Since the test items to be tested by the test instruments Y differ from each other, the reaction completion period for proper testing may differ among the test instruments. Thus, while successively mounting test instruments to the optical measurement apparatus X, the user needs to measure the reaction completion period which differ among the test instruments, and such work is a burden on the user. Such problems related to the reaction time and the time of application of the sample occur also in the testing of a urine test strip, a biochemical test piece and a cuvette type test instrument.

Further, some reagents fixed to the reagent retaining portion 92 may fade or change its color to become lighter when unduly long time lapses after the color development due to the reaction with a sample. In rate assay in which the color development speed per unit time is measured, information on the time at which the color development starts is important. In this case, therefore, when the test instrument Y, to which the sample is applied, is accidentally left for a long time, proper test results may not be obtained when the test instrument X is mounted to the immunochromatography apparatus X.

Patent Document 1: International Publication WO2006/059694

Patent Document 2: JP-A-09-127120

Patent Document 3: JP-A-2001-318101

Patent Document 4: JP-A-2006-250787

DISCLOSURE OF THE INVENTION

Problems to be Solved by the Invention

The present invention has been proposed under the circumstances described above. It is, therefore, an object of the present invention to provide an optical measurement apparatus capable of efficiently performing a test by optical measurement and preventing an erroneous test.

Means for Solving the Problems

According to the present invention, there is provided an optical measurement apparatus to be used with at least one test instrument mounted to the apparatus. The test instrument includes a carrier provided with at least one reagent retaining portion which retains a reagent, and a sample is applied to the carrier. The optical measurement apparatus comprises a reader for reading color development of the reagent retaining portion, and a controller for performing driving control of the reader and determination. The controller performs the determination by utilizing data obtained by reading the color development of the reagent after the lapse of a reaction completion period from the mounting of the test instrument. The reaction completion period depends on the reagent. When the controller detects that color development is completed at the reagent retaining portion before the lapse of the reaction completion period from the mounting of the test instrument, the controller stops the test for the test instrument. The "reaction completion period" in the present invention refers not only to the period of time which is to be taken before the color change of the reagent due to reaction with a sample stops completely but also to the period of time which is to be taken for the progress of color development to such a degree that the reaction between the sample and the reagent is determined to be sufficient. In the latter case, the color change of the reagent may continue even after the lapse of the reaction completion period.

In a preferred embodiment of the present invention, the controller utilizes the result of reading of the reagent retaining portion performed by the reader for the first time after the mounting of the test instrument to determine whether or not color development is completed.

In a preferred embodiment of the present invention, the reagent retaining portion includes a test reagent retaining portion for making a determination with respect to a test item and a confirmation reagent retaining portion for confirming proper movement of the sample through the carrier. When the controller detects that color development is completed at the confirmation reagent retaining portion before the lapse of the reaction completion period from the mounting of the test instrument, the controller stops the test for the test instrument.

In a preferred embodiment of the present invention, the reaction completion period is set by reading the test item information recorded on the test instrument and utilizing the test item information.

In a preferred embodiment of the present invention, the optical measurement apparatus further comprises a sensor for detecting the mounting of the test instrument.

In a preferred embodiment of the present invention, the apparatus is so designed that a plurality of test instruments can be mounted.

In a preferred embodiment of the present invention, the apparatus is so designed that the plurality of test instruments are mounted in a row. The reader scans the plurality of test instruments in a direction in which the row extends.

In a preferred embodiment of the present invention, the reader performs scanning after the mounting of the test instruments and before the lapse of the reaction completion period.

In a preferred embodiment of the present invention, the test instrument is a test piece for immunochromatography, the carrier comprises a porous film, and the reagent retaining portion is provided by fixing an immunologic substance to the porous film.

In a preferred embodiment of the present invention, the test instrument is a test strip to be dipped in a liquid, the carrier comprises a porous film, and the reagent retaining portion is provided by fixing an immunologic substance in a dry state to the porous film.

In a preferred embodiment of the present invention, the test instrument is a test piece which is so designed that a sample is to be dropped onto the reagent retaining portion. The carrier comprises at least one of a high polymer compound and a porous film. The reagent retaining portion is provided by fixing the reagent in a dry state to at least one of the high polymer compound and the porous film.

In a preferred embodiment of the present invention, the test instrument is a light-transmitting cuvette including a plurality of compartments. The carrier comprises a light-transmitting compartment. The reagent retaining portion is provided by sealing the reagent in a liquid or solid state in the compartment.

Other features and advantages of the present invention will become more apparent from the detailed description given below with reference to the accompanying drawings.

BRIEF DESCRIPTION OF THE DRAWINGS

FIG. 6 is a plan view of the sheet showing the results of the test by the optical measurement apparatus shown in FIG. 1.

BEST MODE FOR CARRYING OUT THE INVENTION

Preferred embodiments of the present invention will be described below with reference to the accompanying drawings, using an immunochromatography test instrument as an example.

Figure 1:
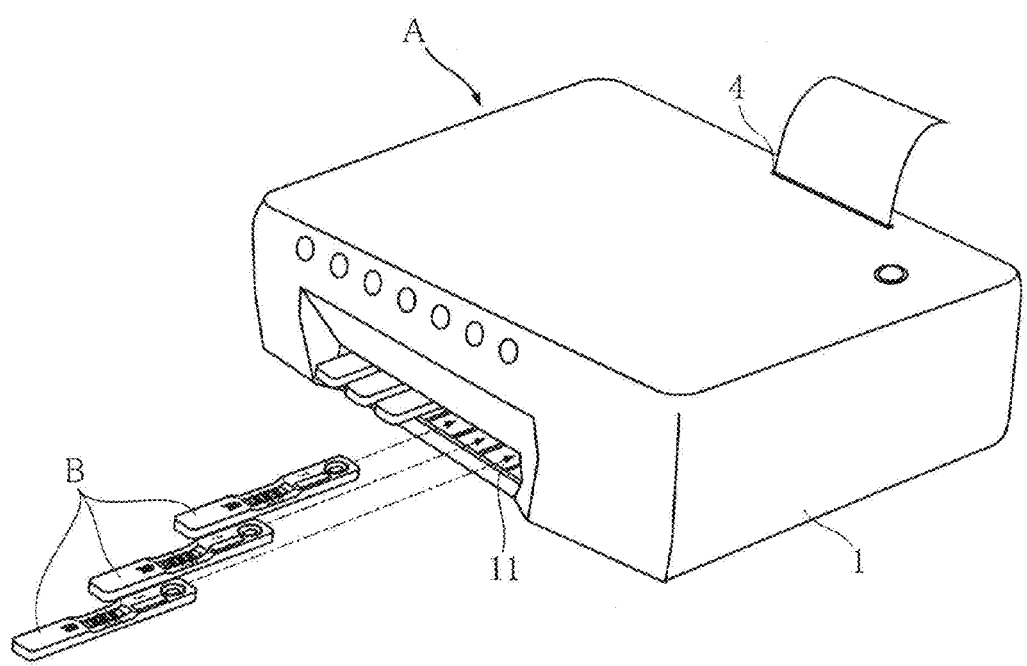
FIG. 1 is an overall perspective view showing an example of optical measurement apparatus according to the present invention.
Figure 2:
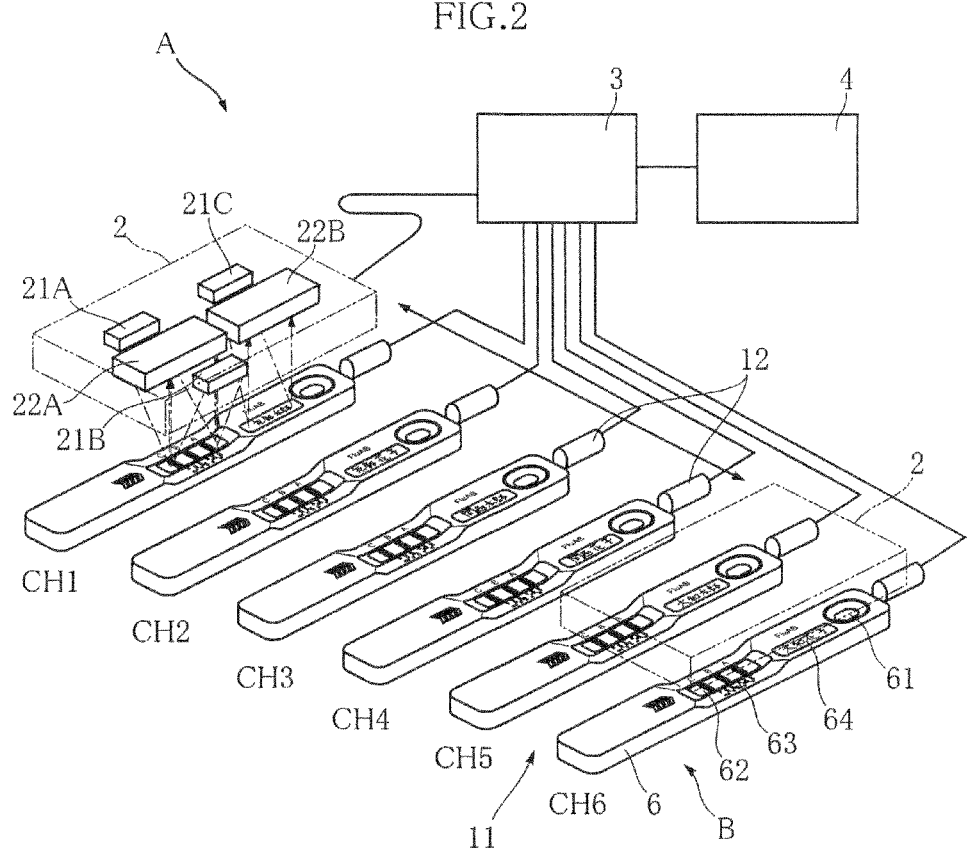
FIG. 2 is a system structure diagram of the optical measurement apparatus shown in FIG. 1.

FIGS. 1 and 2 show an example of optical measurement apparatus according to the present invention. The optical measurement apparatus A of this embodiment includes a case 1, a reader 2, a controller 3 and a printer 4. The apparatus is designed to perform a test by immunochromatography by reading a test instrument B mounted to the apparatus. In FIG. 2, the illustration of the case 1 is omitted for easier understanding.

Figure 3:
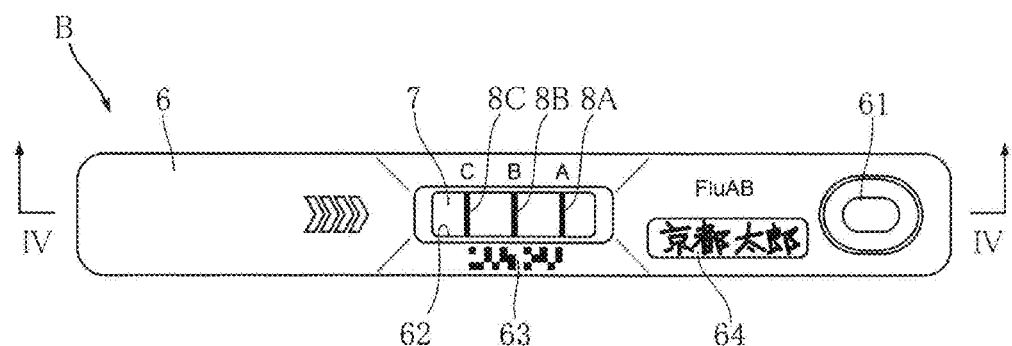
FIG. 3 is a plan view showing an example of test piece to be mounted to the optical measurement apparatus of FIG. 1.
Figure 4:
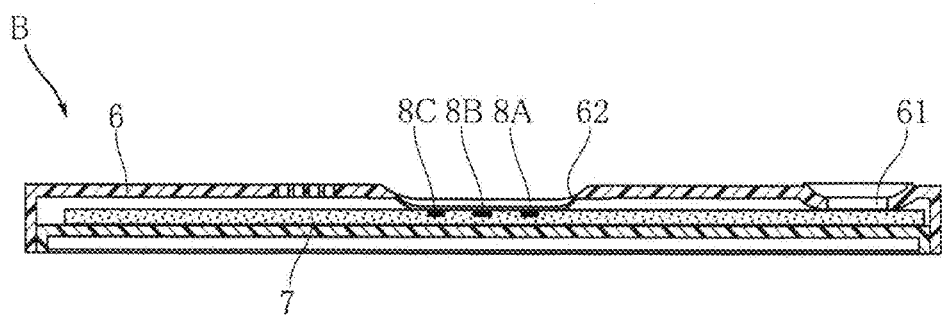
FIG. 4 is a sectional view taken along lines IV-IV in FIG. 3.

FIGS. 3 and 4 show a test instrument B to be mounted to the optical measurement apparatus A. In the test instrument B, a sample applied to the instrument reacts with a reagent. The test instrument has a shape and size suitable for the testing using the optical measurement apparatus A. The test instrument B includes a case 6, a carrier 7 and reagent retaining portions 8A, 8B, 8C to which an immunologic substance such as an antibody is fixed. The test instrument B illustrated in the figure is of a type to be used for e.g. tests for influenza.

The case 6 has an elongated shape, is made of e.g. a white resin, and accommodates the carrier 7 made of a porous matrix. The case 6 includes an application portion 61, a measurement window 62, a test item code 63 and a patient information entry section 64. The application portion 61 is a portion to which a sample is to be applied. The application portion includes a through-hole exposing an end of the carrier 7 and a crater-shaped portion surrounding the through-hole. The measurement window 62 includes an elongated through-hole formed at the center of the case 6 and exposes the reagent retaining portions 8A, 8B, 8C formed at the carrier 7. The test item code 63 is provided for indicating the test item which can be tested by the test instrument B and may be a printed barcode (two-dimensional code in the figure). The patient information entry section 64 is a region in which information such as the name of the patient who is taking the test is to be written by hand.

Figure 8:
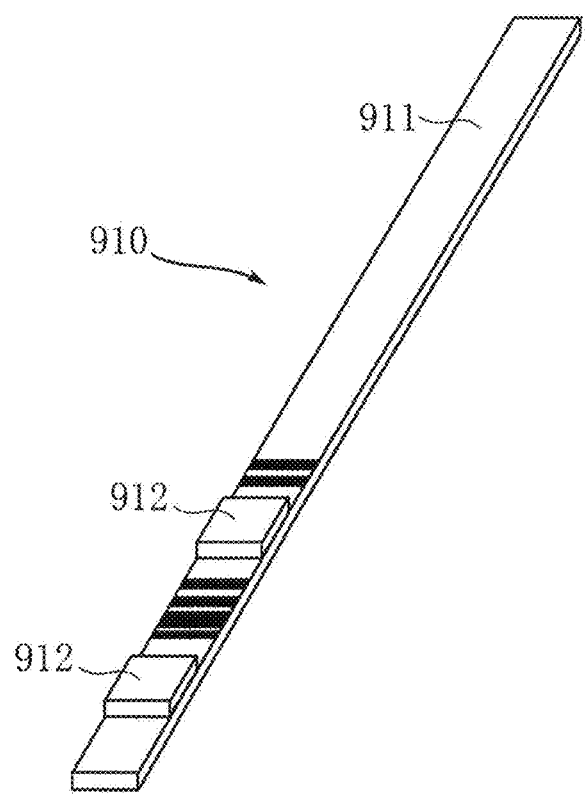
FIG. 8 is a perspective view showing an example of conventional test instrument of a test strip type.
Figure 9:
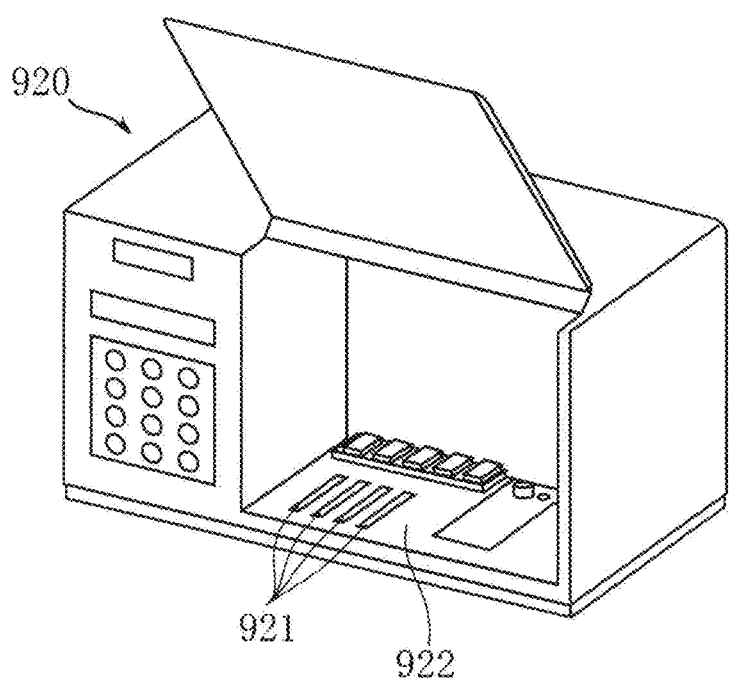
FIG. 9 is a perspective view showing an example of conventional optical measurement apparatus.
Figure 10:
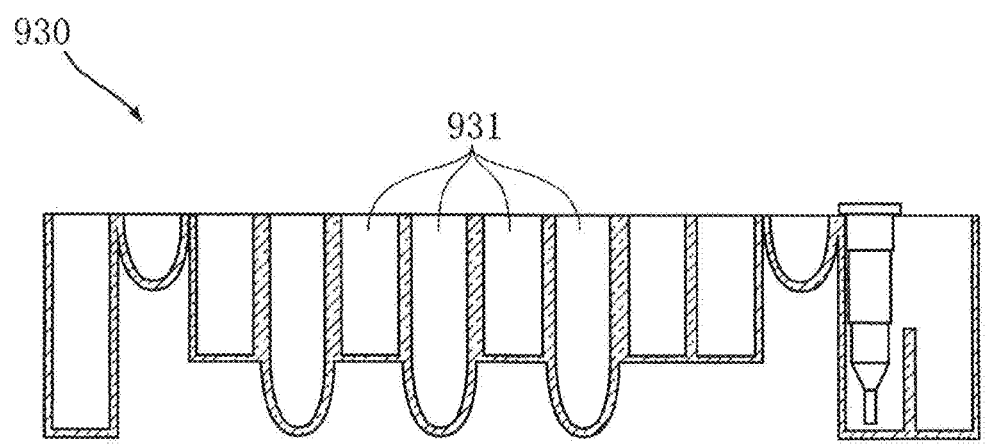
FIG. 10 is a sectional view showing an example of conventional test instrument of a cuvette type.

Though not illustrated, when the test instrument B is a urine test strip, the case 6 may not be necessary. In this instance, the test instrument B includes a base and reagent retaining portions 8A and 8B formed on the base. Each of the reagent retaining portions 8A and 8B is structured as a reagent pad provided by impregnating and drying a reagent in a carrier. The reagent retaining portions are designed for the testing of a plurality of items such that the reagent retaining portion 8A is for testing glucose while the reagent retaining portion 8B is for testing protein, for example. The reagent retaining portions 8A and 8B are similar to the reagent retaining portion 912 shown in FIG. 8. A test item code 63 is printed on the base to show what kind of items the test instrument B measures. For instance, the ideal reaction completion period for each of the reagent retaining portions 8A and 8B is recorded in the test item code 63.

When the test instrument B is of a cuvette type, each of the compartments (hereinafter referred to as "well") in the cuvette corresponds to the carrier 7. By sealing a reagent in a liquid or solid state in the wells, the wells function as reagent retaining portions 8A and 8B. A test item code 63 may be printed on the surface of an aluminum laminate which hermetically seals the well to prevent the content from leaking out of the well. A patient information entry section 64 may also be provided on the surface of the seal.

In a test instrument B for immunochromatography, the carrier 7 is a porous member for causing the sample applied to the application portion 61 to spread over the reagent retaining portions 8A, 8B and 8C and may include a strip made of e.g. nitrocellulose. In a urine test strip, a biochemical test piece or a cuvette-type test instrument, the carrier 7 is a pad made of at least one of a porous body and a high molecular compound impregnated with a reagent or a well constituting the cuvette.

In this embodiment which employs immunochromatography as an example, the reagent retaining portions 8A, 8B, 8C are provided by fixing a reagent (immunologic substance such as an antibody) to part of the carrier 7. Specifically, the reagent retaining portions 8A and 8B are provided by fixing e.g. a reagent for determining positive or negative in tests for influenza. The reagent retaining portions 8A and 8B extend linearly in the width direction of the carrier 7 and are generally called a test line (test reagent retaining portion). The number of reagent retaining portions 8A and 8B may be increased as desired depending on the target to be tested. Although these reagent retaining portions are generally called "test line", they may not be linear but may be in the form of a spot. In a urine test strip, the reagent retaining portion 8A is a reagent pad for testing a single item. Theoretically, therefore, when a urine test strip includes ten reagent retaining portions, ten items can be tested with the urine test strip.

The reagent retaining portion 8C is utilized for determining whether or not the sample has properly passed through the reagent retaining portions 8A and 8B, which are the test lines. Generally, the reagent retaining portion 8C is called a control line (confirmation reagent retaining portion). The reagent retaining portion 8C is provided by fixing e.g. a reagent which develops a color due to reaction with a sample and extends linearly in the width direction of the carrier 7.

As shown in FIG. 1, the case 1 of the optical measurement apparatus A, which may be made of e.g. a resin or a metal, accommodates the reader 2, the controller 3 and the printer 4, which are the other structural elements of the optical measurement apparatus A. The case 1 includes a mount portion 11. A test instrument B to which a sample is applied is to be mounted to the mount portion 11. In this embodiment, the mount portion 11 is made up of six sections CH1-CH6 so that six test instruments B at the most can be mounted at a desired timing. A plurality of LED lamps are provided directly above the mount portion 11. When a test instrument B is mounted to the mount portion 11 at a position directly below one of the LED lamps, the LED lamp emits light of a predetermined color to indicate the mounting of the test instrument. When the test of the test instrument B is completed, the LED lamp emits light of a predetermined color to indicate the completion of the test. As shown in FIG. 2, six sensors 12 are provided at the mount portion 11. The sensors 12 are utilized for determining to which of the sections CH1-CH6 the test instrument B is mounted.

As shown in FIG. 2, the reader 2 includes light emitting modules 21A, 21B, 21C and light receiving sensor modules 22A, 22B. The light emitting modules 21A, 21B and the light receiving sensor module 22A are utilized for reading the reagent retaining portions 8A, 8B, 8C through the measurement window 62 of the test instrument B and reading the test item code 63. The light emitting module 21C and the light receiving sensor module 22B are utilized for reading the patient information entry section 64. In the reader 2, the light emitting modules 21A, 21B, 21C and the light receiving sensor modules 22A, 22B may be supported and driven collectively. Alternatively, for instance, the light emitting modules 21A, 21B and the light receiving sensor module 22A may be supported and driven separately from the light emitting module 21C and the light receiving sensor module 22B.

The light emitting modules 21A and 21B incorporate e.g. LEDs and emit light of different wavelengths. Each of the light emitting modules 21A and 21B emits linear light extending in the longitudinal direction of the test instrument B. The light receiving sensor module 22A may include a plurality of photodiodes arranged in a row or an optical sensor such as an area sensor and generates an output corresponding to the luminance of the received light. The light receiving area of the light receiving sensor module 22A is in the form of a narrow strip extending in the longitudinal direction of the test instrument B. In this embodiment, when the reader 2 is positioned directly above a test instrument B, the light receiving sensor module 22A faces the measurement window 62, and the light emitting modules 21A and 21B emit light toward the measurement window 62 at an angle of about 45 degrees from the opposite sides of the light receiving sensor module 22A. By selectively irradiating the reagent retaining portions 8A, 8B, 8C with light of different wavelengths from the light emitting modules 21A and 21B, the reagent retaining portions can be read as image data of at least two kinds of color phases.

The light emitting module 21C incorporates e.g. an LED and emits light of a predetermined wavelength. Specifically, the light emitting module 21C emits linear light extending in the longitudinal direction of the test instrument B. The light receiving sensor module 22B may include a plurality of photodiodes arranged in a row or an optical sensor such as an area sensor and generates an output corresponding to the luminance of the received light. The light receiving area of the light receiving sensor module 22B is in the form of a narrow strip extending in the longitudinal direction of the test instrument B. In this embodiment, when the reader 2 is positioned directly above a test instrument B, the light receiving sensor module 22B faces the patient information entry section 64, and the light emitting module 21C emits light toward the patient information entry section 64 at an angle of about 45 degrees.

The reader 2 is reciprocally movable directly above the six test instruments B mounted to the mount portion 11. Specifically, the reader is slidably supported by a guide bar (not shown) extending in the direction in which the six test instruments B are arranged and driven by a driving means such as a motor, a pulley or a belt (all not shown). When the reader 2 reciprocates directly above the six test instruments B, the light emitting modules 21A, 21B and the light receiving sensor module 22A read the measurement window 62 and the test item code 63 of the six test instruments B alternately. At the same time, the light emitting module 21C and the light receiving sensor module 22B successively read the patient information entry sections 64 of the six test instruments B. Even when only five or less test instruments B are mounted to the mount portion 11, the reader 2 properly performs the reading operation with respect to the mounted test instruments B.

For instance, the controller 3 includes a CPU, a ROM, a RAM and an interface. The CPU controls the entirety of the optical measurement apparatus A. The ROM stores various programs or parameters for the processing to be performed by the CPU. The RAM temporarily stores programs or measurement results. The interface performs the inputting and outputting operations of the controller 3.

The printer 4 is a device for outputting the test results of the test instrument B and incorporates e.g. a thermal printhead. As shown in FIG. 6, when the test of the test instruments B is completed in the immunochromatography apparatus A, the test results corresponding to the test item are printed.

As an example of test using the optical measurement apparatus A, tests for influenza by immunochromatography will be described below.

Figure 5:
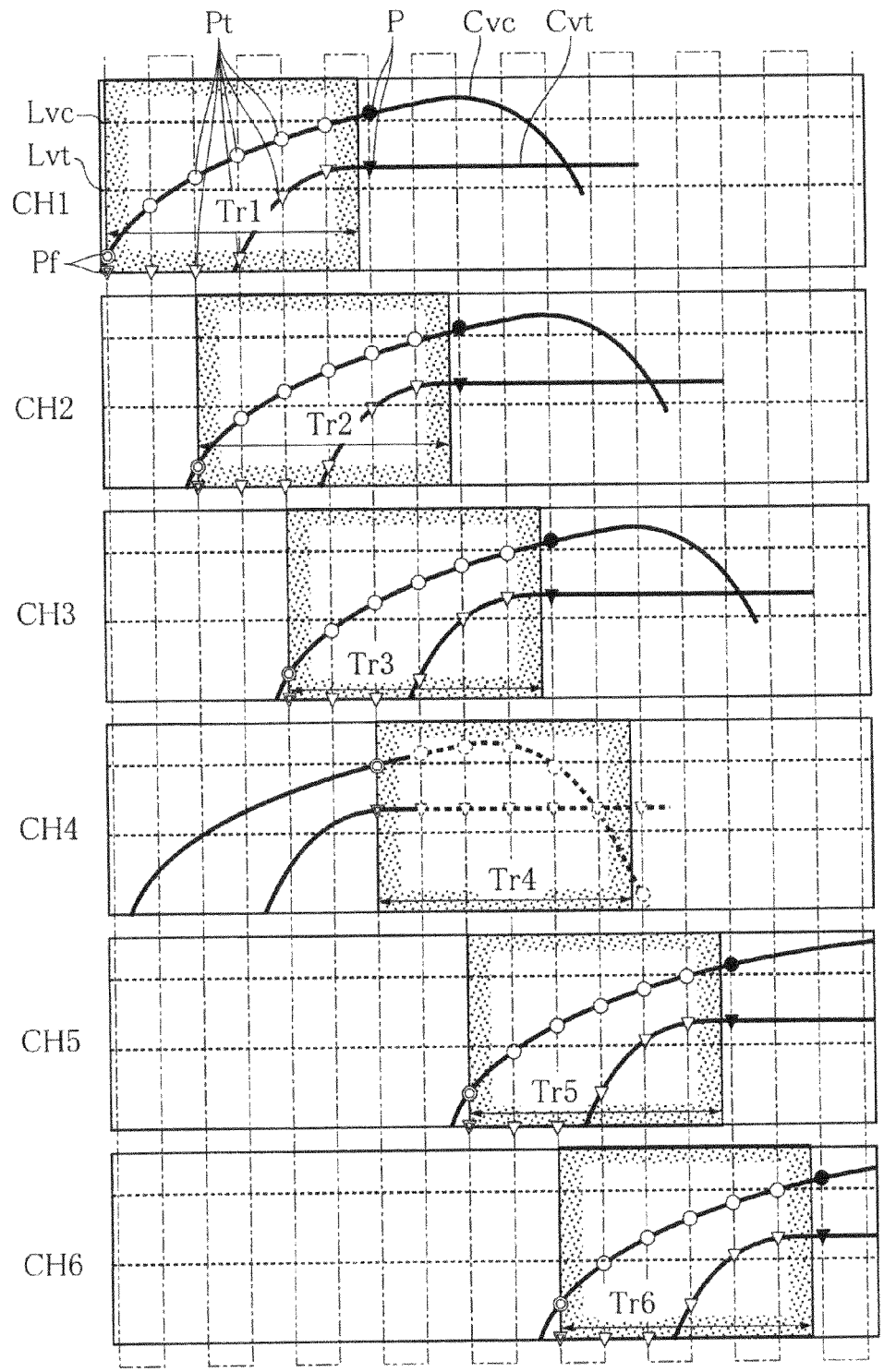
FIG. 5 is a chart showing an example of test by the optical measurement apparatus shown in FIG. 1.
Figure 7:
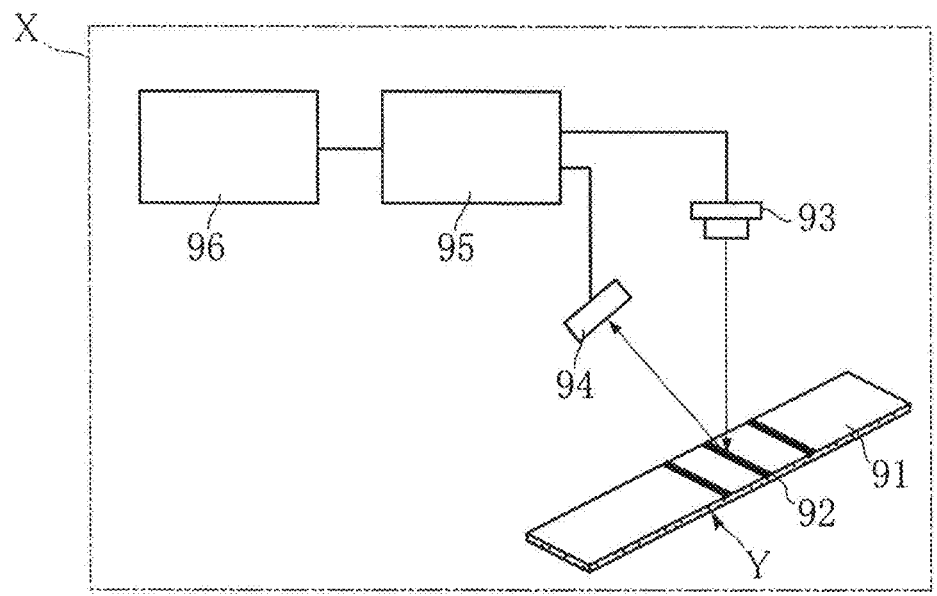
FIG. 7 is a system structure diagram of an example of conventional optical measurement apparatus.

FIG. 5 shows an example of test performed using the optical measurement apparatus A. In this figure, the horizontal axis indicates time, and the reaction progress curves Cvc and Cvt indicate the progress of reaction in the test pieces 6 mounted to the sections CH1-CH6. Specifically, the reaction progress curves Cvc indicate the degree of progress of the reaction at the reagent retaining portions 8A and 8B, which are the test lines, whereas the reaction progress curves Cvt indicate the degree of progress of the reaction at the reagent retaining portions 8C, which are the control lines.

The reference levels Lvc and Lvt represented by the dotted lines in the figure indicate the degree of reaction above which determination for a certain item is possible. Specifically, when a reaction progress curve Cvc exceeds the reference level Lvc, whether the sample is positive or negative for influenza is properly determined from the color development state. When a reaction progress curve Cvt exceeds the reference level Lvt, it is determined that the sample applied to the application portion 61 has reached the reagent retaining portion 8C through the reached the reagent retaining portion 8A and 8B in the carrier 7. In this example, even when the sample is actually positive, the color of the reagent retaining portions 8A and 8B developed due to the reaction with the sample changes to indicate negative after the lapse of much time. In such a case, as shown in the figure, the reaction progress curve Cvc falls below the reference level Lvc again. This unduly changed state of color development is not suitable for the test determination.

The single-dashed lines in the figure indicate the trajectory of the reciprocal movement of the reader 2 over the sections CH1-CH6. In this example, tests for influenza are performed with respect to six patients. Specifically, samples taken from six patients are applied to the respective test instruments B, and the test instruments B are successively mounted to the mount portion 11. In each of the six test instruments B, the name of the patient is written in the patient information entry section 64.

First, the test instrument B to which sample is first applied is mounted to the section CH1 of the mount portion 11. The sensor 12 detects the mounting of this test instrument and transmits a mount signal to the controller 3. When the reader 2 passes above the test instrument B in the section CH1 for the first time, the reader performs a reading operation Pf (indicated by the double circle and the double triangle in the figure) to read the reagent retaining portions 8A, 8B, 8C and the test item code 63.

The test instrument B in the section CH1 is a test instrument mounted immediately after the application of the sample. Thus, color development of the reagent retaining portion 8C is not observed in the results of analysis of the image data of the reagent retaining portion 8C obtained by the reading operation Pf. In this case, the controller 3 determines that the test instrument is in proper condition, i.e., the sample has not reached the reagent retaining portion 8C, which is a control line, and continues the subsequent test processing.

In accordance with the test item represented by the test item code 63, the controller 3 sets a reaction completion period Tr1 for the section CH1. After the mounting of the test instrument to the section CH is detected by the sensor 12, the reader 2 performs a reading operation Pt (indicated by circles and triangles in the figure) a plurality of times, i.e., every time it passes over the section CH1 until the reaction completion period Tr1 lapses. In this reading operations Pt, reading of the reagent retaining portions 8A, 8B, 8C is repeated. In this example, however, the results of the reading operation performed during the reaction completion period Tr1 are not used for the determination. Instead, the results of the reading operation P (indicated by the black circles and the black triangles in the figure) for reading the fix portions 8A, 8B, 8C which is performed for the first time after the lapse of the reaction completion period Tr1 is used for the determination of the influenza test. At the time point of the reading operation P, the reaction progress curve Cvc is above the reference level Lvc, because the reaction completion period Tr1 has lapsed since the mounting of the test instrument B to the section CH1.

While the test processing for the section CH1 is performed in the above-described manner, the test processing for the sections CH2-CH6 is also performed. In this embodiment, the test item is the same for all the test instruments B in the sections CH1-CH6, so that reaction completion periods Tr1-Tr6 are the same. Thus, the reading operation is performed successively with respect to the sections CH1-CH6 in the order of mounting.

Herein, attention is to be focused on the test instrument B mounted to the section CH4. The test instrument B is not mounted through a proper process. That is, the test instrument B is left for a while after the sample application without being immediately mounted. Thus, before the test instrument is mounted to the section CH4, the sample has reached the reagent retaining portion 8C through the reagent retaining portions 8B and 8C in the carrier 7. Thus, from the results of the reading operation Pf, the controller 3 finds that color development of the reagent retaining portion 8C is completed. In this case, the controller 3 stops the test processing for this test instrument B and does not perform the reading operations Pt and P after the reading operation Pf.

In measurement by immunochromatography, when the application of a sample to a test instrument B and the mounting of the test instrument to the optical measurement apparatus A are successively performed properly, the optical measurement apparatus A needs to wait for a while until the sample completes the movement through the reagent retaining portions 8A, 8B and 8C in the carrier 7. Thus, a waiting time (hereinafter referred to as "movement continuation time"), which is necessary for the sample to move sufficiently, is set in the controller 3. In this embodiment, whether the movement of the sample is unduly completed is determined based on the color development of the reagent retaining portion 8C in the reading operation Pf, which is performed when the reader 2 passes over the test instrument B for the first time after the mounting of the test instrument B. That is, in this embodiment, the movement continuation time is set to the period from when the reader 2 passes over the test instrument B until the time when the reader passes the test instrument next time. However, unlike this embodiment, whether the movement of the sample is completed may be determined based on the color development of the reagent retaining portion 8C detected by a certain reading operation Pt. The movement continuation time can be set appropriately by selecting any one of the reading operations Pt as the base for the determination. However, the movement continuation time does not exceed the reaction completion period Tr1-Tr6.

As shown in FIG. 6, the test results of the samples obtained from the six patients are successively printed by the printer 4. The content to be printed includes the date and time, the identification number, the mount section (any of CH1-CH6), the test item, the test result and the name written in the patient information entry section 64. As for the patient name, the image data of the patient information entry section 64 read by the light receiving sensor module 22B of the reader 2 is printed. To achieve clearer printing, the image data of the patient information entry section 64 may appropriately be subjected to image processing such as binarization by the controller 3. In this embodiment, the test instrument B in the section CH4 is determined to be mounted through an improper process. Thus, the letters "NG" are printed at the portion for showing the test results of this test instrument B.

The advantages of the optical measurement apparatus A will be described below.

According to the embodiment, it is possible to immediately mount a test instrument B to the optical measurement apparatus A after a sample is applied to the test instrument B. That is, after a sample is applied to the test instrument B, the user does not need to measure the time until the test becomes possible. Thus, the user can successively perform other works such as the application of a sample to another test instrument B. The test instrument B mounted to the optical measurement apparatus A is properly tested after the lapse of an appropriate time period. Thus, the optical measurement apparatus A enhances the efficiency of the test.

Generally, when a test instrument B is left by mistake after the sample application, proper test results are not obtained from the test instrument B. According to this embodiment, by checking the color development of the reagent retaining portion 8C immediately after the mounting of a test instrument, the test is prevented from proceeding with respect to a test instrument B left improperly like the test instrument B in the section CH4 shown in FIG. 5.

The reaction completion period Tr1-Tr6 is set automatically by reading the test item code 63. Thus, the user does not need to manually input the reaction completion period Tr1-Tr6 in accordance with the test item. By the operation of the sensors 12, the controller 3 grasps the accurate time at which each test instrument B is mounted. Thus, the measurement of the reaction completion period Tr1-Tr6 is automatically started.

In this way, according to the optical measurement apparatus A, the user obtains proper test results just by mounting the test instrument B to the optical measurement apparatus A. Thus, while six test instruments B at the most can be mounted, the user's work does not become complicated. Further, when a test instrument B is left by mistake in spite of considerable attention, such a test instrument B is substantially removed by the optical measurement apparatus A.

As will be understood from the example described above, the optical measurement apparatus A is suitable for performing tests for influenza smoothly and efficiently with respect to a large number of people. Further, even when tests for a plurality of items which require different reaction completion periods, such as influenza and allergy, are to be performed, the work for the tests does not become complicated. The optical measurement apparatus A can automatically perform the operations from the mounting to the outputting of the test results. Thus, as the operation means for the user's operation, to provide e.g. a power button may be sufficient.

Since the reader 2 is designed to successively scan the sections CH1-CH6, the reading operations Pf, Pt, P are performed uniformly with respect to all the test instruments B mounted to the mount portion 11. The reader 2 is designed to collectively read the regions elongated in the longitudinal direction of the test instrument B, i.e., elongated perpendicularly to the scanning direction. Thus, all of the necessary reading operations are performed by the reader's scanning operation through the sections CH1-CH6. Thus, it is not necessary to perform another scanning operation in the longitudinal direction of the test instrument B in addition to the above-described scanning operation. Thus, the reading operation does not require much time. The movement continuation time can be set appropriately, with the time taken for one reciprocal movement of the reader 2 for scanning set as one unit.

The optical measurement apparatus according to the present invention is not limited to the foregoing embodiment. The specific structure of each part of the optical measurement apparatus according to the present invention may be varied in design in many ways. For instance, the number of the reagent retaining portions 8A, 8B, 8C is not limited to three, and a larger number of reagent retaining portions may be provided.

The number of test instruments B to be mounted to the measurement apparatus A is not limited to that of the foregoing embodiment, and may be larger or smaller than six. As the number of the mountable test instruments increases, the efficiency of the test enhances. Even when only one test instrument can be mounted, the apparatus still has the advantage that the user does not need to measure the reaction completion period. Reading the test item code 63 and the patient information entry section 64 by the reader 2 is desirable for automatic testing, though the present invention is not limited to this. When some burden on the user is allowed, the test item or the reaction completion period may be inputted manually by the user. The reader 2 may be modified in structure, as long as the reagent retaining portions 8A, 8B, 8C can be read properly. For instance, the emitted light and the light receiving area may not need to extend in the longitudinal direction of the test instrument B. The optical measurement apparatus of the present invention may be used for various tests in addition to tests by immunochromatography.

The present invention is not limited to the structure in which the reagent retaining portions 8A, 8B as the test reagent retaining portion and the reagent retaining portion 8C as the confirmation reagent retaining portion are provided separately. A reagent retaining portion serving as both the test reagent retaining portion and the confirmation reagent retaining portion may be provided. A reading operation Pf with respect to a certain reagent retaining portion is performed before the reaction completion period lapses. When coloring (color development) is observed at this reagent retaining portion, it is determined that unduly long time has lapsed since the application of the sample, and the test is not performed.

The invention claimed is:

1. An optical measurement apparatus comprising:
   a test instrument including a carrier with a test reagent retaining portion, a confirmation reagent retaining portion, and said carrier capable of being applied with a sample for coloration reaction at the test reagent retaining portion and the confirmation reagent retaining portion;
   a mount portion for mounting the test instrument;
   a sensor for detecting the test instrument mounted at the mount portion;
   a reader for optically reading color development at the test reagent retaining portion and the confirmation reagent retaining portion; and
   a controller for performing driving control of the reader;
   wherein the test instrument includes a test item code that is indicative of a reaction completion period set for the test instrument and stored in the controller as part of parameters,
   wherein the reader is configured to read the test item code for the controller to set the reaction completion period,
   wherein the controller is configured to perform test by utilizing data obtained by reading the color development at the test reagent retaining portion during and after the reaction completion period starting from the mounting of the test instrument at the mount portion,
   wherein the controller is also configured to stop the test when the controller detects that the reading of the color development at the confirmation reagent retaining portion is higher than a first threshold value before lapse of the reaction completion period starting from the mounting of the test instrument at the mount portion, the first threshold value being set for the confirmation reagent retaining portion for storage in the controller as part of parameters, and
   wherein the controller is further configured to continue the test by determining, immediately after the lapse of the reaction completion period, whether the reading of the color development at the test reagent retaining portion is higher than a second threshold value when the controller detects that the color development at the confirmation reagent retaining portion is not higher than the first threshold value before the lapse of the reaction completion period starting from the mounting of the test instrument, the second threshold value being set for the test reagent retaining portion for storage in the controller as part of the parameters and different from the first threshold value.

2. The optical measurement apparatus according to claim 1, wherein the mount portion is configured to mount a plurality of test instruments.

3. The optical measurement apparatus according to claim 2, wherein the plurality of test instruments are mounted in a row on the mount portion; and wherein the reader successively reads the plurality of test instruments in a direction in which the row extends.

4. The optical measurement apparatus according to claim 3, wherein the reader is configured to perform the successive reading after the mounting of the test instruments and before the lapse of the reaction completion period.

5. The optical measurement apparatus according to claim 1, wherein:
   the test instrument is a test piece for immunochromatography;
   the carrier comprises a porous film; and
   the test reagent retaining portion contains an immunologic substance fixed to the porous film as the test reagent.

6. The optical measurement apparatus according to claim 1, wherein:
   the test instrument is a test strip to be dipped in a liquid;
   the carrier comprises a porous film; and
   the test reagent retaining portion contains an immunologic substance fixed to the porous film in a dry state as the test reagent.

7. The optical measurement apparatus according to claim 1, wherein:
   the test instrument is a test piece comprising the test reagent retaining portion to which the sample in liquid form is dropped;
   the carrier comprises at least one of a high polymer compound and a porous film; and
   a test reagent is fixed to at least one of the high polymer compound and the porous film in a dry state.

* * * * *